US00PP30992P2

(12) United States Plant Patent
Van Swieten

(10) Patent No.: US PP30,992 P2
(45) Date of Patent: Oct. 29, 2019

(54) ***PHALAENOPSIS* ORCHID PLANT NAMED 'PHALFAUF'**

(50) Latin Name: ***Phalaenopsis* hybrid**
Varietal Denomination: PHALFAUF

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/998,069

(22) Filed: Jun. 22, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

(56) References Cited

PUBLICATIONS

UPOV-PLUTO: Plant Variety Database Apr. 11, 2019 citation for 'PHALFAUF' (1 page).*
EU Community Plant Variety Rights Application No. 2017/2402, Application n°A201702871, filed Sep. 28, 2017, 8 pages.
EU Community Plant Variety Office Official Gazette, Jun. 2017, Dec. 15, 2017, cover page and pp. 39, 59.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFAUF', particularly characterized by having small, purple striped flowers with white edges and dark red-purple lips, 1 to 3 peduncles that are medium long and sturdy, leaves that are oblong, and is propagated by meristem tissue culture, is disclosed.

3 Drawing Sheets

Genus and species: *Phalaenopsis* hybrid.
Variety denomination: 'PHALFAUF'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFAUF'.

The new *Phalaenopsis* plant is a product of a planned breeding program conducted by the inventor in Bleiswijk, The Netherlands. The objective of this breeding program was to create a new *Phalaenopsis* plant with numerous attractive and unique, small, purple striped flowers with white edges and dark red-purple lips, suitable for potted plant production.

The new *Phalaenopsis* plant 'PHALFAUF' is a result of cross-pollination made by the inventor in March 2008 in Bleiswijk, The Netherlands of the proprietary female, or seed parent, *Phalaenopsis* hybrid '20413-03' (unpatented) with the proprietary male, or pollen parent, *Phalaenopsis* hybrid '01-1787' (unpatented).

The new *Phalaenopsis* was selected by the inventor as a single plant within the progeny of the stated cross-pollination in a controlled greenhouse in Bleiswijk, The Netherlands in April 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 28, 2017. 'PHALFAUF' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFAUF' as a new and distinct variety of *Phalaenopsis* plant.

1) Small, purple striped flowers with white edges and dark red-purple lips;
2) 1 to 3 peduncles;
3) Peduncle is medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 42-week old plants in May 2018. Colors in the photographs may differ from the color values cited in the detailed botanical description, which accurately describe the actual colors of the new variety.

DESCRIPTION OF THE NEW VARIETY

Figure 1:
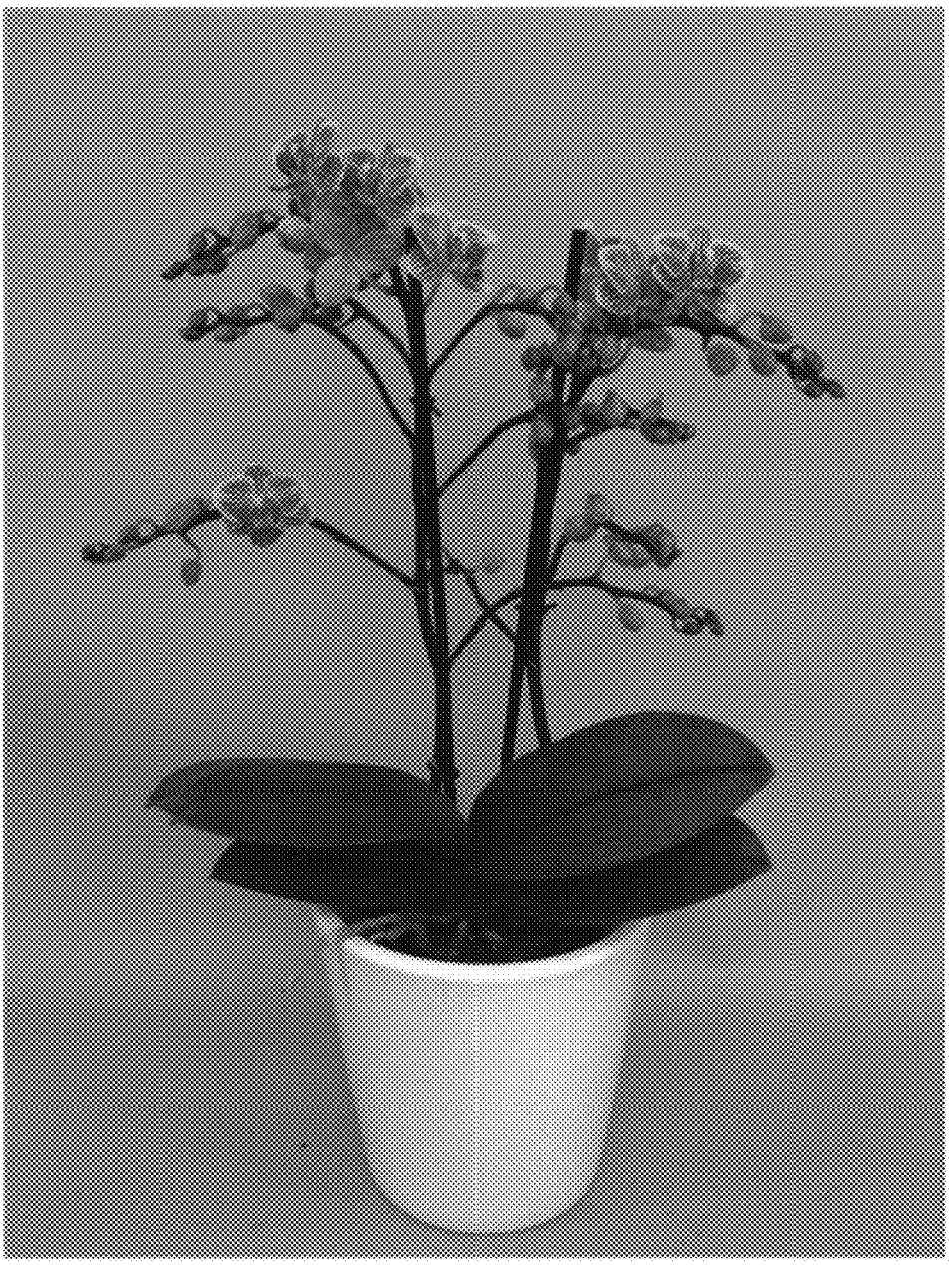
FIG. 1 shows the overall plant habit, including blooms, buds and foliage of 'PHALFAUF'.
Figure 2:
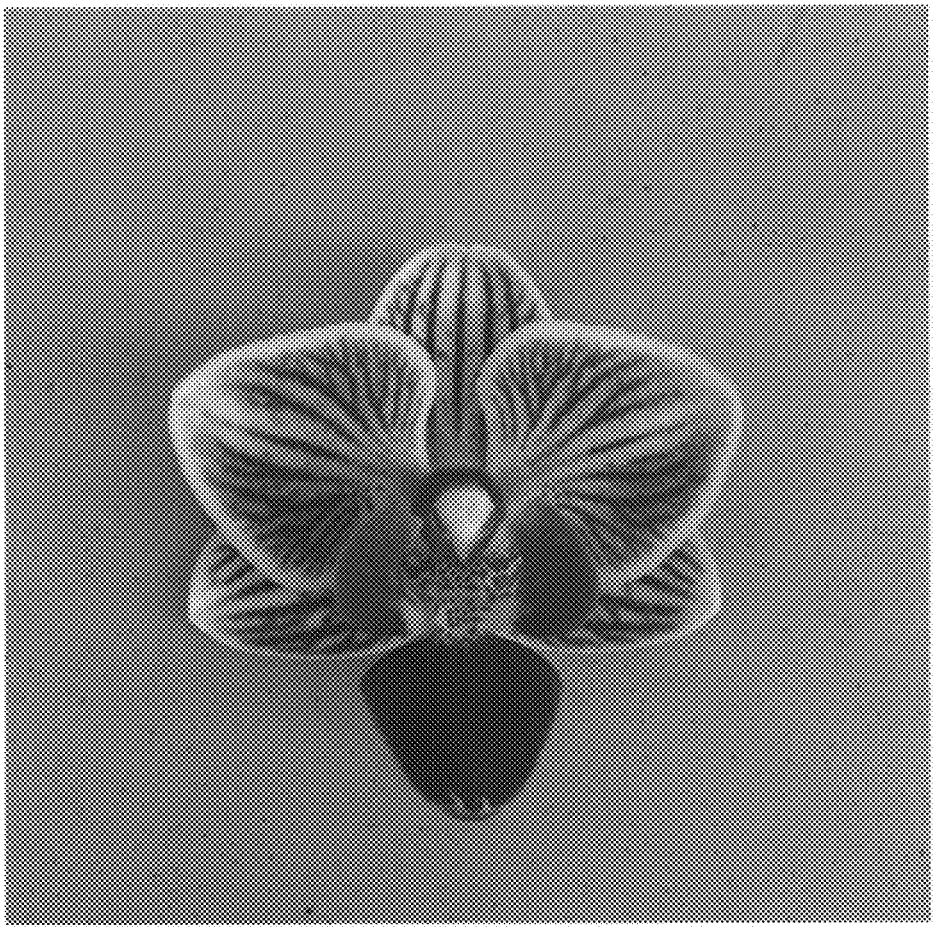
FIG. 2 shows a close-up of a flower of 'PHALFAUF'.
Figure 3:
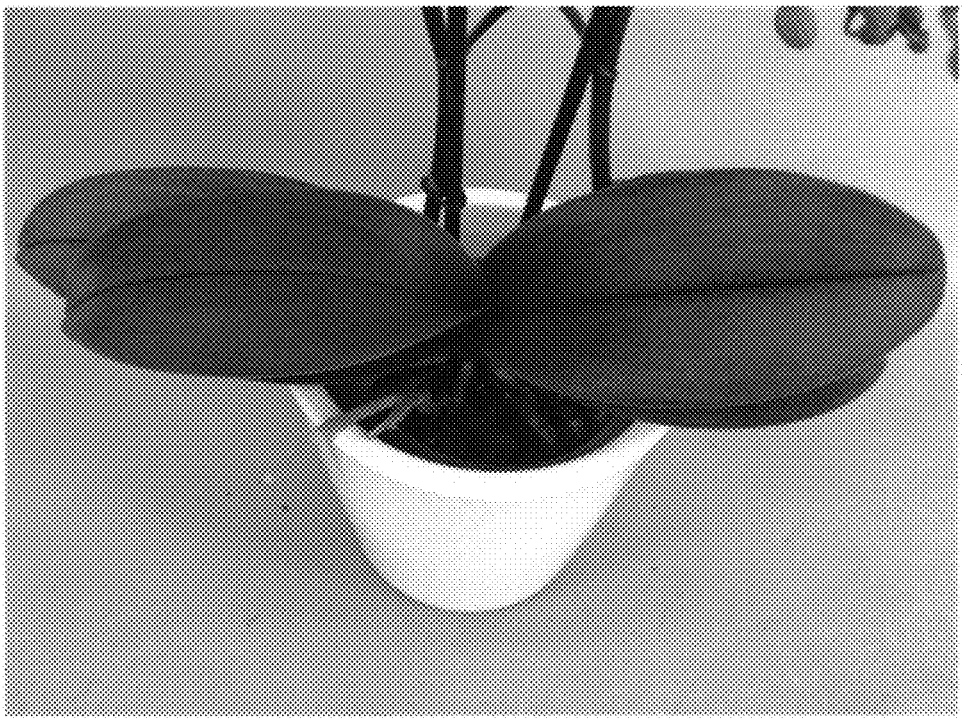
FIG. 3 shows an overhead view of the leaves of 'PHALFAUF'.

The following detailed description sets forth the distinctive characteristics of 'PHALFAUF'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in May 2018 on flowering plants which were planted in 9 centimeter (diameter) pots. After in-vitro propagation, the plants were grown in nursery trays for 18-20 weeks, followed by transplantation to 9 centimeter (diameter) pots and grown in a greenhouse between 27° C. to 29° C. for 25 weeks, continued by a cooling period of 6 weeks between 18° C. to 20° C. and 11 weeks in a greenhouse of 21° C. Flowering occurs after 42-weeks in a 9 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFAUF'.

Parentage:

*Female parent*.—*Phalaenopsis* cultivar '20413-03' (unpatented).

*Male parent*.—*Phalaenopsis* cultivar '01-1787' (unpatented).

Propagation:

*Type*.—Meristem tissue culture.

Roots:

*Root description*.—Greyed-green colored roots (between RHS 190B and 190C) with branching lateral roots having green (RHS 144A) colored root tips.

Plant:

*Commercial crop time to flowering*.—Following asexual propagation (in-vitro), the rooted cuttings grow for 18-20 weeks. After transplantation into 9 cm pots, the plants are finished after 40 to 42 weeks.

*Growth habit of peduncle*.—Standard, green leaves, panicle.

*Height (from soil level to top of inflorescence)*.—Approximately 30.0 cm to 35.0 cm.

*Width (measured from leaf tips)*.—About 24.0 cm to 26.0 cm.

*Vigor*.—Moderate.

Leaves:

*Mature leaves*.—Quantity per plant: 7 to 10 leaves are produced before flowering. Length (fully expanded): 11.0 cm to 13.0 cm. Width: 5.0 cm to 6.0 cm. Shape: Oblong. Base shape: Moderately elongated. Apex: Obtuse unequal. Leaf blade angle with the petiole (measured from the horizontal position): Between 10 degrees and 25 degrees. Leaf margin: Entire. Color: Upper surface: RHS 147A with slightly grey over color (RHS 191C). Lower surface: RHS 147B. Texture (both upper and lower surfaces): Rough. Thickness: 2.1 mm to 2.4 mm. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—25 to 35.

*Length*.—30.0 cm to 35.0 cm.

*Diameter*.—4.2 mm to 4.4 mm.

*Strength*.—Moderate.

*Aspect*.—Upright to slightly pendant.

*Texture*.—Smooth.

*Color*.—Mix of green (RHS 146B) and brown (RHS 200B).

*Internode length*.—3.5 cm to 4.5 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 200.0 mm to 240.0 mm.

*Flowering time*.—First flowers can be expected 7 to 8 months after planting in a 9 cm (diameter) pot.

*Flower*.—Height: 30.0 mm to 32.0 mm. Diameter: 36.0 mm to 38.0 mm. Depth of lip: 16.0 mm to 18.0 mm.

*Flower longevity*.—On the plant: 8 to 14 weeks.

*Fragrance*.—Absent.

*Flower bud*.—Average size: Small to medium. Length: 12.0 mm to 14.0 mm. Width: 9.0 mm to 11.0 mm. Shape: Egg shaped. Color: Yellow-green (RHS 145A) at the base; light purple (RHS 76A) with dark purple-red stripes (between RHS N79B and N79C) toward the tip.

*Petals*.—Arrangement: Open/free. Shape: Semi-circular. Apex: Obtuse asymmetric. Margin: Entire. Length (from base to tip): 16.0 mm to 18.0 mm. Width: 18.0 mm to 20.0 mm. Color (when fully opened): Upper surface: Basic color: Purplish-pink (RHS N78C). Over color: Reddish-purple stripes (RHS N78A) and white edge (RHS NN155C). Lower surface: Basic color: Light reddish-purple (RHS N78D). Over color: Reddish-purple (RHS N78B) with white edge (RHS NN155C).

*Dorsal sepal*.—Shape: Elliptic. Apex: Obtuse; the tip curves toward the front. Margin: Entire. Length (from base to tip): 19.0 mm to 21.0 mm. Width: 14.0 mm to 16.0 mm. Color (when fully opened): Upper surface: Basic color: Very light purple (RHS 76C). Over color: Purplish-pink (RHS N78C) and reddish-purple stripes (RHS N78A) with white edge (RHS NN155C). Lower surface: Basic color: Very light purple (RHS 76B). Over color: Reddish-purple stripes (RHS N78B) with white edge (RHS NN155C).

*Lateral sepals*.—Shape: Ovate. Apex: Obtuse asymmetric. Margin: Entire. Length (from base to tip): 19.0 mm to 21.0 mm. Width: 13.0 mm to 15.0 mm. Color (when fully opened): Upper surface: Basic color: Very light purple (RHS 76D). Over color:

Reddish-purple spots (RHS N78B) at the base; purplish-pink (RHS N78C) and reddish-purple stripes (RHS N78A) toward the margin; small white edge (RHS NN155C). Lower surface: Basic color: Very light purple (RHS 76B). Over color: Diluting reddish-purple stripes (RHS N78B) and white edge (RHS NN155C).

*Labellum* (*lip*).—Whiskers: Present, very short. Length of whiskers: 0.0 mm to 2.0 mm. Color of whiskers: Reddish-purple (RHS N78A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 11.0 mm to 13.0 mm. Width: 7.0 mm to 9.0 mm. Color: Upper surface: Slightly yellow (RHS 13A) with dark red stripes (RHS 59A) at the base; dark red region (RHS 59A) on one side; reddish-purple (RHS N78A) toward margin. Lower surface: Very light purple (RHS 76D) with a dark red region (RHS 59A) on the front side.

*Apical lobe*.—Shape: Ovate. Margin: Entire. Length: 14.0 mm to 16.0 mm. Width: 12.0 mm to 14.0 mm. Color: Upper surface: Dark red (RHS 59A) at the base; reddish-purple (RHS N78A) toward whiskers. Lower surface: Very light purple (RHS 76D) with a dark red region (RHS 59A) on the front side.

*Callus*.—Average size: Small. Height: 3.0 mm to 4.0 mm. Length: 3.0 mm to 4.0 mm. Width: 2.0 mm to 3.0 mm. Color: Yellow (RHS 13A) dotted (RHS 59A).

Reproductive organs:

*Column*.—Length: 7.0 mm to 9.0 mm. Diameter: 3.2 mm to 3.4 mm. Color: Reddish-purple (RHS N78A).

*Pollinia*.—Quantity: 2. Diameter: 0.7 mm to 0.9 mm. Color: Orange (RHS 24A).

*Ovary*.—Length: 7.0 mm to 9.0 mm. Diameter: 1.4 mm to 1.6 mm.

*Pedicel*.—Length: 22.0 mm to 24.0 mm. Diameter: 1.6 mm to 1.8 mm. Color: Light yellow-green (RHS 145D) and purplish-red (RHS N77B).

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFAUF' differs from female parent plant '20413-03' (unpatented) in that 'PHALFAUF' has a striped and edged flower pattern, an obtuse dorsal sepal apex and apical lobes that are dark red at the base and reddish-purple toward the whiskers, whereas '20413-03' has an edged flower pattern, an emarginated dorsal sepal apex and dark red apical lobes. Additionally, 'PHALFAUF' has smaller flowers than '20413-03'.

'PHALFAUF' differs from male parent plant '01-1787' (unpatented) in that 'PHALFAUF' has a larger depth of lip than '01-1787'.

'PHALFAUF' is most similar to the commercial *Phalaenopsis* plants named 'PHALDYQ' (unpatented) and 'PHALDONFI' (U.S. Plant Pat. No. 26,066). 'PHALFAUF' differs from the commercial variety 'PHALDYQ' in that 'PHALFAUF' has an obtuse dorsal sepal apex and whiskers, whereas 'PHALDYQ' has a rounded to slightly emarginated dorsal sepal apex and no whiskers. Additionally, 'PHALFAUF' has smaller flowers than 'PHALDYQ'.

'PHALFAUF' differs from the commercial variety 'PHALDONFI' in that 'PHALFAUF' has an obtuse dorsal sepal apex, whereas 'PHALDONFI' has an emarginated dorsal sepal apex. Additionally, 'PHALFAUF' has smaller flowers and shorter whiskers than 'PHALDONFI'.

I claim:

1. A new and distinct variety of *Phalaenopsis* plant named 'PHALFAUF', substantially as described and illustrated herein.

* * * * *